United States Patent
Erden

(10) Patent No.: US 11,810,651 B2
(45) Date of Patent: Nov. 7, 2023

(54) MULTI-DIMENSIONAL MAPPING OF BINARY DATA TO DNA SEQUENCES

(71) Applicant: SEAGATE TECHNOLOGY LLC, Cupertino, CA (US)

(72) Inventor: Mehmet Fatih Erden, St. Louis Park, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 1167 days.

(21) Appl. No.: 16/117,742

(22) Filed: Aug. 30, 2018

(65) Prior Publication Data

US 2019/0073446 A1 Mar. 7, 2019

Related U.S. Application Data

(60) Provisional application No. 62/553,496, filed on Sep. 1, 2017.

(51) Int. Cl.

| G16B 30/00 | (2019.01) |
|---|---|
| G16B 50/30 | (2019.01) |
| G16B 50/40 | (2019.01) |
| G16B 50/00 | (2019.01) |
| G16B 5/00 | (2019.01) |
| G11C 13/02 | (2006.01) |
| B82Y 10/00 | (2011.01) |
| B82Y 15/00 | (2011.01) |
| C12Q 1/6874 | (2018.01) |
| C12Q 1/6869 | (2018.01) |

(52) U.S. Cl.
CPC .............. *G16B 50/00* (2019.02); *G11C 13/02* (2013.01); *G16B 5/00* (2019.02); *G16B 30/00* (2019.02); *G16B 50/30* (2019.02); *G16B 50/40* (2019.02); *B82Y 10/00* (2013.01); *B82Y 15/00* (2013.01); *C12Q 1/6869* (2013.01); *C12Q 1/6874* (2013.01)

(58) Field of Classification Search
CPC ........ G16B 50/00; G16B 30/00; G16B 50/30; G16B 50/40; G11C 13/02
See application file for complete search history.

(56) References Cited

U.S. PATENT DOCUMENTS

| 7,056,724 B2 | 6/2006 | Wong et al. | |
|---|---|---|---|
| 2004/0153255 A1 | 8/2004 | Ahn | |
| 2015/0261664 A1 | 9/2015 | Goldman et al. | |
| 2018/0253528 A1* | 9/2018 | Strauss | G16B 30/00 |
| 2019/0362814 A1* | 11/2019 | Roquet | G16B 30/20 |

OTHER PUBLICATIONS

Branton, D., Deamer, D., Marziali, A. et al. The potential and challenges of nanopore sequencing. Nat Biotechnol 26, 1146-1153 (2008). (Year: 2008).*
Rocha, A.S.L.L., Faria, L.C.B., Kleinschmidt, J.H., Palazzo, R. and Silva-Filho, M.C., Jun. 2010. DNA sequences generated by $\mathbb{Z}$ 4-linear codes. In 2010 IEEE International Symposium on Information Theory (pp. 1320-1324). IEEE (Year: 2010).*
Le Goff, S.Y., 2003. Signal constellations for bit-interleaved coded modulation. IEEE Transactions on Information Theory, 49(1), pp. 307-313 (Year: 2003).*
de Oliveira, H.M. and Santos-Magalhães, N.S., The Genetic Code Revisited: Inner-to-outer map, 2D-Gray map, and World-map Genetic Representations. arXiv preprint arXiv:1503.02570. (Year: 2015).*
Holmes, I. Modular non-repeating codes for DNA storage. arXiv preprint arXiv:1606.01799. p. 1-41. (Year: 2016).*

* cited by examiner

*Primary Examiner* — Lori A. Clow
*Assistant Examiner* — Janna Nicole Schultzhaus
(74) *Attorney, Agent, or Firm* — HOLZER PATEL DRENNAN

(57) ABSTRACT

Systems and methods for multi-dimensional mapping of binary data DNA sequences are described. In one embodiment, the method may include determining a current level of a first DNA base from a sequence of DNA bases based at least in part on a read process of the sequence, determining a current level of a second DNA base after the first DNA base and a current level of a third DNA base after the second DNA base, and decoding binary data from the sequence based at least in part on the determined current level of the first DNA base, the determined current level of the second DNA base, and/or the determined current level of the third DNA base.

20 Claims, 12 Drawing Sheets

MULTI-DIMENSIONAL MAPPING OF BINARY DATA TO DNA SEQUENCES

RELATED APPLICATIONS

This application claims the benefit of the filing date of U.S. Provisional Application No. 62/553,496, filed on 1 Sep. 2017, and entitled MULTI-DIMENSIONAL MAPPING OF BINARY DATA TO DNA SEQUENCES, the disclosure of which is incorporated in its entirety by this reference.

SUMMARY

The present disclosure is directed to methods and systems for multi-dimensional mapping of deoxyribonucleic acid (DNA) sequences. In one embodiment, the present techniques provide a mapping between DNA bases (also referred to as DNA nucleotides) and binary bits of user data (e.g., compressed data, uncompressed data, encoded data, decoded data, etc.). In some embodiments, the present techniques may include a fixed-length multi-dimensional mapping between binary data bits and DNA bases that yields a bit/base ratio at or relatively near a theoretical limit and that improves a Signal-to-Noise Ratio (SNR) and/or a Bit-Error-Rate (BER) associated with the multi-dimensional mapping. In some cases, the present techniques may increase a storage density of a DNA storage system based at least in part on the multi-dimensional fixed length mapping of DNA sequences A deoxyribonucleic acid (DNA) storage system for multi-dimensional mapping of binary data to DNA sequences is described. In one embodiment, the DNA storage system device may include one or more storage mediums, including DNA storage mediums, and one or more hardware processors to perform the mapping of the binary data to DNA sequences. In some embodiments, the one or more hardware processors may generate a mapping between the binary data and DNA bases, convert the binary data to a sequence of DNA bases based at least in part on the mapping, and store the sequence of DNA bases in a DNA storage medium. In some embodiments, the DNA storage system may include a DNA reader for reading sequences of DNA bases. In some examples, the DNA reader may be configured to determine a current level of a first DNA base from a sequence of DNA bases based at least in part on a read process of the sequence, determine a current level of a second DNA base after the first DNA base and a current level of a third DNA base after the second DNA base, and decode binary data from the sequence based at least in part on the determined current level of the first DNA base, the determined current level of the second DNA base, and/or the determined current level of the third DNA base. In some cases, determining the current level of the second DNA base and/or third DNA base may be based at least in part on performing the read process. Additionally or alternatively, determining the current level of the second DNA base and/or third DNA base may be based at least in part on a set of possible DNA base pairs permitted to occur after the first DNA base. In some cases, the set of possible DNA base pairs permitted to occur after the first DNA base may be determined at least in part by an encoding scheme that does not allow homopolymers to occur in adjacent DNA bases.

In some cases, the set of possible DNA base pairs permitted to occur after the first DNA base includes nine possible combinations of DNA base pairs based at least in part on the encoding scheme not allowing homopolymers. In some cases, the nine possible combinations of DNA base pairs map to nine nodes of a signal constellation diagram. In some examples, the DNA reader may be further configured to remove one of the nine possible combinations of DNA base pairs based at least in part on reducing a maximum number of node neighbors for each of the remaining eight nodes of the signal constellation diagram to two node neighbors, resulting in eight possible combinations of DNA base pairs permitted to occur after the first DNA base in the encoding scheme.

In some cases, the encoding scheme may include mapping each of the remaining eight possible combinations of DNA base pairs to one of eight 3-bit binary values. In some cases, each of the eight possible combinations of DNA base pairs may be uniquely mapped to one of the 3-bit binary values. In some cases, the read process may be based at least in part on detecting blocked ionic current from passing the sequence through a nano-pore (e.g., certain nucleotides blocking more ionic current than other nucleotides). In some examples, a different current output may occur for each DNA base of the sequence as it passes through the nano-pore. In one example, each DNA base of the sequence may be one of Adenine, Guanine, Cytosine, or Thymine.

In some cases, the encoding scheme may be configured to encode binary data into DNA bases arranged in a particular order, the sequence being arranged according to the encoding scheme. In some cases, each possible second DNA base may follow directly after the first DNA base in the sequence. In some cases, each possible third DNA base may follow directly after the second DNA base in the sequence. In some cases, a location of the first DNA base may occur at a start of or after the start of the sequence.

An apparatus for multi-dimensional mapping of binary data to DNA sequences is also described. In one embodiment, the apparatus may include a processor, memory in electronic communication with the processor, and instructions stored in the memory, the instructions being executable by the processor to perform the steps of generating a mapping between the binary data and deoxyribonucleic acid (DNA) bases, converting the binary data to a sequence of DNA bases based at least in part on the mapping, and storing the sequence of DNA bases in a DNA storage medium. In some cases, the apparatus may include a DNA reader configured to determine a current level of a first DNA base from a sequence of DNA bases based at least in part on a read process of the sequence, determine a current level of a second DNA base after the first DNA base and a current level of a third DNA base after the second DNA base, and decode binary data from the sequence based at least in part on the determined current level of the first DNA base, the determined current level of the second DNA base, and/or the determined current level of the third DNA base. In some cases, determining the current level of the second DNA base and/or third DNA base may be based at least in part on performing the read process. Additionally or alternatively, determining the current level of the second DNA base and/or third DNA base may be based at least in part on a set of possible DNA base pairs permitted to occur after the first DNA base. In some cases, the set of possible DNA base pairs permitted to occur after the first DNA base may be determined at least in part by an encoding scheme that does not allow homopolymers to occur in adjacent DNA bases.

A method for multi-dimensional mapping of binary data to DNA sequences is also described. In one embodiment, the method may include generating a mapping between the binary data and deoxyribonucleic acid (DNA) bases, converting the binary data to a sequence of DNA bases based at least in part on the mapping, and storing the sequence of DNA bases in a DNA storage medium. In some cases, the method may include determining a current level of a first DNA base from a sequence of DNA bases based at least in part on a read process of the sequence, determining a current level of a second DNA base after the first DNA base and a current level of a third DNA base after the second DNA base, and decoding binary data from the sequence based at least in part on the determined current level of the first DNA base, the determined current level of the second DNA base, and/or the determined current level of the third DNA base. In some cases, determining the current level of the second DNA base and/or third DNA base may be based at least in part on performing the read process. Additionally or alternatively, determining the current level of the second DNA base and/or third DNA base may be based at least in part on a set of possible DNA base pairs permitted to occur after the first DNA base. In some cases, the set of possible DNA base pairs permitted to occur after the first DNA base may be determined at least in part by an encoding scheme that does not allow homopolymers to occur in adjacent DNA bases.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Figure 1:
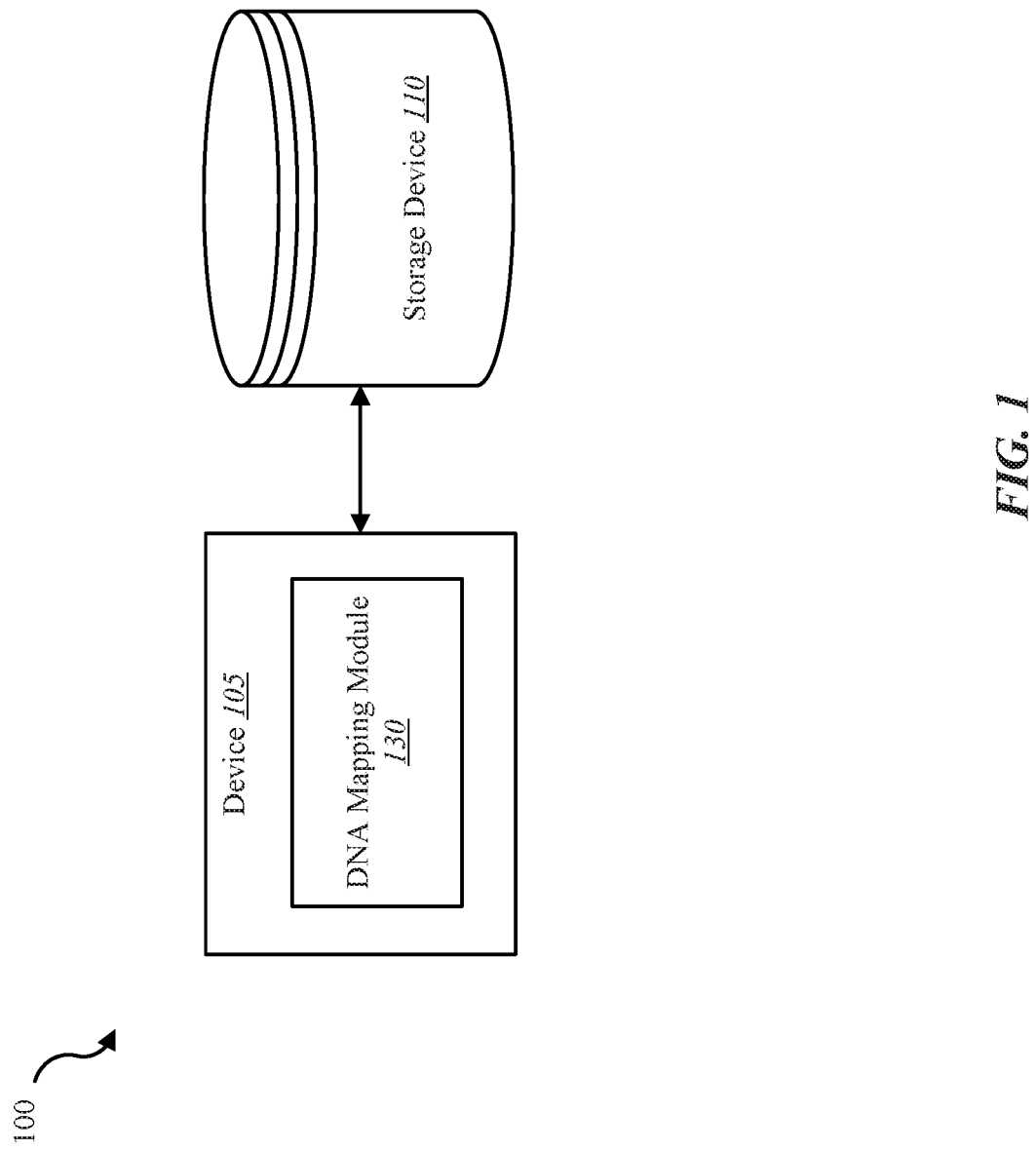
FIG. 1 is a block diagram of an example of a system in accordance with various embodiments.

The following relates generally to multi-dimensional mapping of binary data DNA sequences. The demand for data storage is increasing exponentially. As a result, alternative storage methods are attracting more and more attention. Because of its relatively high storage density potential, deoxyribonucleic acid (DNA) storage is one alternative storage method attracting attention. In one example, a storage density greater than $10^{21}$ bits/cm$^3$ may be achieved when individual DNA molecules are used to store binary bits of user data, a significantly higher storage density than is currently available.

Conventional solutions include using Huffman coding to convert a byte (8-bit) to 5 or 6 ternary digits and then using rotating nucleotide encoding to map the converted byte to DNA sequences. However, conventional solutions do not approach the mapping problem from a signal constellation perspective, and do not make any definitive effort to optimize system Signal-to-Noise Ratio (SNR) or a Bit-Error-Rate (BER) while optimizing the mapping efficiency. In contrast, the present techniques may include a fixed-length multi-dimensional mapping (e.g., constellation mapping, constellation diagram, etc.) between binary data bits and DNA bases that yields a bit/base ratio at or relatively near a theoretical limit and that improves the Signal-to-Noise Ratio (SNR) and/or a Bit-Error-Rate (BER) associated with the multi-dimensional mapping.

One or more read processes for DNA storage currently exist. In one example, a DNA molecule may include the four nucleic acids or bases (referred to generally as nucleotides) Adenine (A), Guanine (G), Cytosine (C), and Thymine (T). In this example, a DNA strand may pass through a nano-pore of a lipid membrane. As the DNA strand passes through the nano-pore, the bases of the DNA sequence may at least partially block an ionic current that flows through the nano-pore. Variations in how much ionic current is blocked may result from different bases passing through the nano-pore. In one embodiment, the present techniques may be based at least in part on a DNA read process where, in one non-limiting example, Adenine (A) may yield the highest current output, followed by Cytosine (C), then Thymine (T), and finally Guanine (G).

In one example of the present techniques, a homopolymer may be a run of two or more identical bases such as AA, CC, TT, or GG in a DNA sequence. In one embodiment, the present techniques may configure a DNA sequence without homopolymers. In some cases, homopolymers may be associated with higher error rates in DNA storage in conventional solutions. As nucleotides in a strand of DNA are read by a DNA read process, measured values associated with each nucleotide passed through the DNA reader (e.g., variations in measured ionic current flow) may result in ambiguity as to which nucleotide was passed through the DNA reader. In one example, if a drop of 1 picoamps (PA) indicates adenine and a drop of 2 picoamps indicates cytosine, and the DNA reader indicates a drop of 1.5 picoamps, an ambiguity arises as to whether the read nucleotide is adenine or cytosine. The DNA reader may register such an ambiguity as a read error. Accordingly, the present techniques reduce such errors by implementing a fixed-length multi-dimensional mapping between binary data bits and DNA bases that yields a bit/base ratio at or relatively near a theoretical limit and that improves a Signal-to-Noise Ratio (SNR) and/or a Bit-Error-Rate (BER) associated with the multi-dimensional mapping. Some embodiments of the present techniques maximize the bit/base in the absence of homopolymers. Since absence of homopolymers limits consecutive identical bases, there are three options for each base (e.g., A can be followed by C, T, or G, but not A, etc.). This means that the theoretical limit for bit/base of the present techniques may be equal to $\log_2 (3)=1.585$.

In one embodiment, the present techniques may provide a multi-dimensional fixed length mapping of DNA sequences. In some cases, the present techniques provide a mapping between DNA bases and binary bits of user data (e.g., compressed data, uncompressed data, encoded data, decoded data, etc.). In some embodiments, the present techniques may yield a bit/base ratio close to a theoretical limit. In some cases, the present techniques optimize a Signal-to-Noise Ratio (SNR) and/or a Bit-Error-Rate (BER) of a DNA storage system. In some cases, the present techniques may improve a capacity of a DNA storage system based at least in part on the multi-dimensional fixed length mapping of DNA sequences.

A first alternative embodiment to the present techniques may assume homopolymers and maximize bit/base. In the first alternative embodiment, there may be four current levels for a given set of signal levels. In one example, a highest signal level may be associated with DNA base Adenine (A), a second highest current level of the signal levels may be associated with DNA base Cytosine (C), a third highest current level of the signal levels may be associated with DNA base Thymine (T), and a lowest current level of the signal levels may be associated with DNA base Guanine (G). The first alternative embodiment may include using 2-bit encoding to encode data to those four levels. In some cases, there may be multiple ways of assigning those 2-bit combinations. For example, there may be 4! or 4*3*2*1=24 possible mappings of 2-bits to 4 levels. In one embodiment, first alternative embodiment may include mapping the four current levels based on Gray Coding. Using Gray Coding may limit the number of bits changing between adjacent levels to a single bit, which may result in reducing the BER of the DNA storage system. In one embodiment, only 8 of the 24 possible mappings of 2-bits to 4 levels may satisfy the maximum 1-bit change between adjacent levels. In one embodiment, the first alternative embodiment may include using at least one of the following 8 possible mapping combinations:

A=[00], C=[01], T=[11], G=[10]
A=[00], C=[10], T=[11], G=[01]
A=[01], C=[11], T=[10], G=[00]
A=[01], C=[00], T=[10], G=[11]
A=[10], C=[11], T=[01], G=[00]
A=[10], C=[00], T=[01], G=[11]
A=[11], C=[01], T=[00], G=[10]
A=[11], C=[10], T=[00], G=[01]

A second alternative embodiment to the present techniques may assume no homopolymers with 1 bit/base. In the second alternative embodiment, A or C may map to zero, and G or T may map to 1. In the second alternative embodiment, an encoding of binary data to DNA bases may start with mapping an initial binary 0 to DNA base A and mapping an initial binary 1 to DNA base G. For example, when a sequence of bits starts with a binary 0, then the encoded DNA sequence begins with DNA base A, and when a sequence of bits starts with a binary 1, then the encoded DNA sequence begins with DNA base G. In some cases, the second alternative embodiment may include toggling between A and C for consecutive binary 0s (e.g., an encoding of binary sequence 000 may be ACA, etc.), and toggling between G and T for consecutive binary 1s (e.g., an encoding of binary sequence 111 may be GTG, etc.). In some cases, when a transition occurs, the second alternative embodiment may include assigning G for a transition from binary 0 to binary 1, and assigning A for a transition from binary 1 to binary 0. In some cases, the second alternative embodiment may include ensuring maximum signal change when a transition between 0 and 1 occurs, thus maximizing SNR of the DNA storage system.

FIG. 1 is a block diagram illustrating one embodiment of an environment 100 in which the present techniques may be implemented. The environment may include device 105 and storage device 110. The storage device 110 may include any combination of DNA storage drives, hard disk drives, solid state drives, and/or hybrid drives that include a DNA storage drive as well as a hard disk drive and/or a solid state drive. In some embodiments, the systems and methods described herein may be performed on a single device such as device 105. In some cases, the methods described herein may be performed on multiple storage devices or a network of storage devices.

Examples of device 105 include a DNA storage system, a DNA read system, a DNA encoding system, a DNA decoding system, one or more computing devices, one or more processors of a computing system, a storage server, a storage enclosure, a storage controller, storage drives in a distributed storage system, storage drives on a cloud storage system, storage devices on personal computing devices, storage devices on mobile computing devices, storage devices on a server, or any combination thereof. In some configurations, device 105 may include DNA mapping module 130. In one example, the device 105 may be coupled to storage device 110. In some embodiments, device 105 may be a component of a host of the storage device 110 such as an operating system, host hardware system, or any combination thereof.

In one embodiment, device 105 may include one or more computing devices that each includes one or more processors, memory, and/or one or more storage devices. In some cases, device 105 may include a wireless storage device. In some embodiments, device 105 may include a cloud drive for a home or office setting. In one embodiment, device 105 may include a network device such as a switch, router, access point, or any combination thereof. In one example, device 105 may be operable to receive data streams, store and/or process data, and/or transmit data from, to, or in conjunction with one or more local and/or remote computing devices.

The device 105 may include a database. In some cases, the database may be internal to device 105. In some embodiments, storage device 110 may include a database. Additionally, or alternatively, the database may include a connection to a wired and/or a wireless database. Additionally, as described in further detail herein, software and/or firmware (for example, stored in memory) may be executed on one or more processors of device 105. Such software and/or firmware executed on the one or more processors may be operable to cause the device 105 to monitor, process, summarize, present, and/or send a signal associated with the operations described herein.

In some embodiments, storage device 110 may connect to device 105 via one or more networks. Examples of networks include cloud networks, local area networks (LAN), wide area networks (WAN), virtual private networks (VPN), a personal area network, near-field communication (NFC), a telecommunications network, wireless networks (using 802.11, for example), and cellular networks (using 3G and/or LTE, for example), or any combination thereof. In some configurations, the network may include the Internet and/or an intranet. The device 105 may receive and/or send signals over a network via a wireless communication link. In some embodiments, a user may access the functions of device 105 via a local computing device, remote computing device, and/or network device. For example, in some embodiments, device 105 may include an application that interfaces with a user. In some cases, device 105 may include an application that interfaces with one or more functions of a network device, remote computing device, and/or local computing device.

In one embodiment, the storage device 110 may be internal to device 105. As one example, device 105 may include a storage controller that interfaces with storage media of storage device 110. DNA mapping module 130 may generate a fixed-length multi-dimensional mapping between binary data bits and DNA bases. In some cases, the multi-dimensional mapping generated by DNA mapping module 130 may yield a bit/base ratio at or relatively near a theoretical limit. In some cases, the multi-dimensional mapping generated by DNA mapping module 130 may improve a Signal-to-Noise Ratio (SNR) and/or a Bit-Error-Rate (BER) associated with a DNA storage system and/or an implementation of the multi-dimensional mapping.

Figure 2:
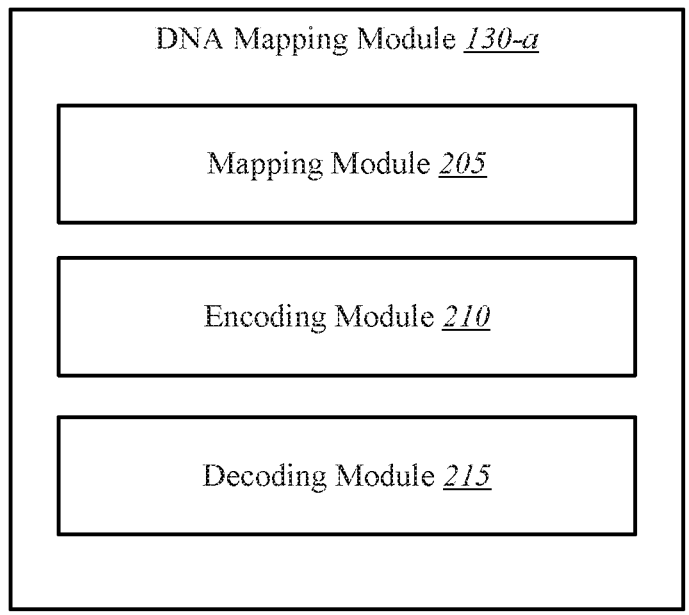
FIG. 2 shows a block diagram of one or more modules in accordance with various aspects of this disclosure.

FIG. 2 shows a block diagram of DNA mapping module 130-a. The DNA mapping module 130-a may include one or more processors, memory, and/or one or more storage devices. The DNA mapping module 130-a may include mapping module 205, encoding module 210, and decoding module 215. The DNA mapping module 130-a may be one example of DNA mapping module 130 of FIG. 1. Each of the illustrated components may be in communication with each other.

In one embodiment, DNA mapping module 130-a may enable systems and methods to store user data in sequences of DNA bases. In one embodiment, mapping module 205 may generate a mapping between DNA bases and binary bits. In some cases, mapping module 205 may generate a multi-dimensional mapping between DNA bases and binary bits. In some cases, the multi-dimensional mapping generated by mapping module 205 may enable a bit/base ratio at or relatively near a theoretical limit. In some cases, the multi-dimensional mapping generated by mapping module 205 may improve a Signal-to-Noise Ratio (SNR) and/or a Bit-Error-Rate (BER) associated with a DNA storage system and/or an implementation of the multi-dimensional mapping.

In one embodiment, encoding module 210 may receive a sequence of binary bits of data (e.g., 0010010001011001, etc.) and store the sequence of binary bits in a DNA storage system. In some cases, encoding module 210 may transform the sequence of binary bits and store the transformed sequence of binary bits in the DNA storage system. For example, encoding module 210 may encode a sequence of binary bits of data into a sequence of DNA bases (e.g., T,A,C,G,A,T,G, etc.).

In one embodiment, decoding module 215 may receive a read request. Upon receiving the read request, decoding module 215 may access the DNA storage medium to retrieve at least a portion of data stored in the DNA storage medium. In one example, decoding module 215 may fetch a sequence of DNA bases stored in the DNA storage medium based at least in part on the read request. In one embodiment, decoding module 215 may transform the fetched sequence of DNA bases to read the data encoded in the sequence of DNA bases. As one example, decoding module 215 may decode the fetched sequence of DNA bases into a sequence of binary bits of data.

Figure 3:
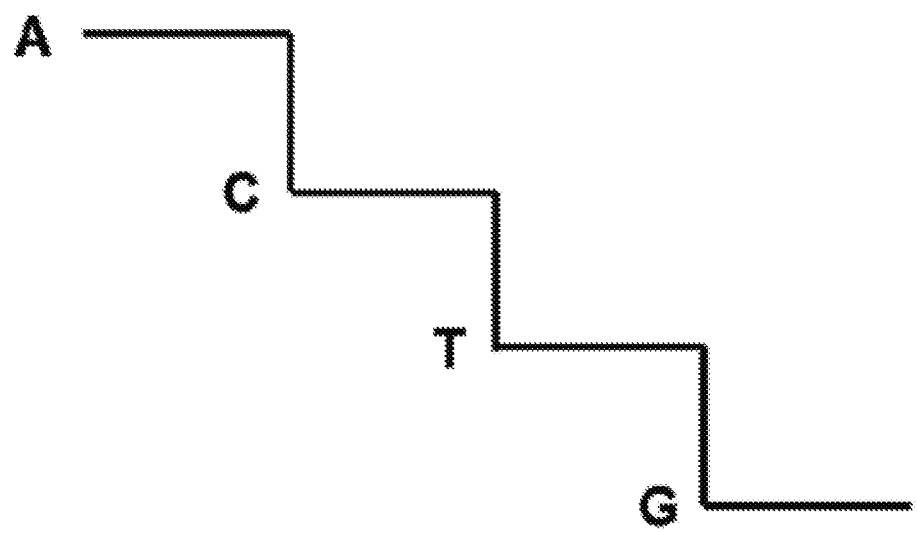
FIG. 3 shows a diagram of signal levels in accordance with various aspects of this disclosure.

FIG. 3 shows a diagram of signal levels 300 in accordance with various aspects of this disclosure. The signal levels 300 may be associated with a multi-dimensional mapping of DNA sequences, in accordance with various examples. In some cases, signal levels 300 may be configured by DNA mapping module 130 of FIGS. 1 and/or 2. In one embodiment, signal levels 300 may be configured based at least in part on an ionic current through a nano-pore of a lipid membrane. In some cases, signal levels 300 may be referred to as current levels.

As illustrated, DNA mapping module 130 may configure a highest current level of the signal levels 300 associated with DNA base Adenine (A), a second highest current level of the signal levels 300 associated with DNA base Cytosine (C), a third highest current level of the signal levels 300 associated with DNA base Thymine (T), and a lowest current level of the signal levels 300 associated with DNA base Guanine (G). The illustrated signal levels 300 depict one example of a signal level configuration in relation to a DNA storage system. For example, in some embodiments, the present techniques may use a configuration where Cytosine, Thymine, or Guanine is the highest current level; where Adenine, Thymine, or Guanine is the second highest current level; where Adenine, Cytosine, or Guanine is the third highest current level; and/or where Adenine, Cytosine, or Thymine is the lowest current level.

Figure 4:
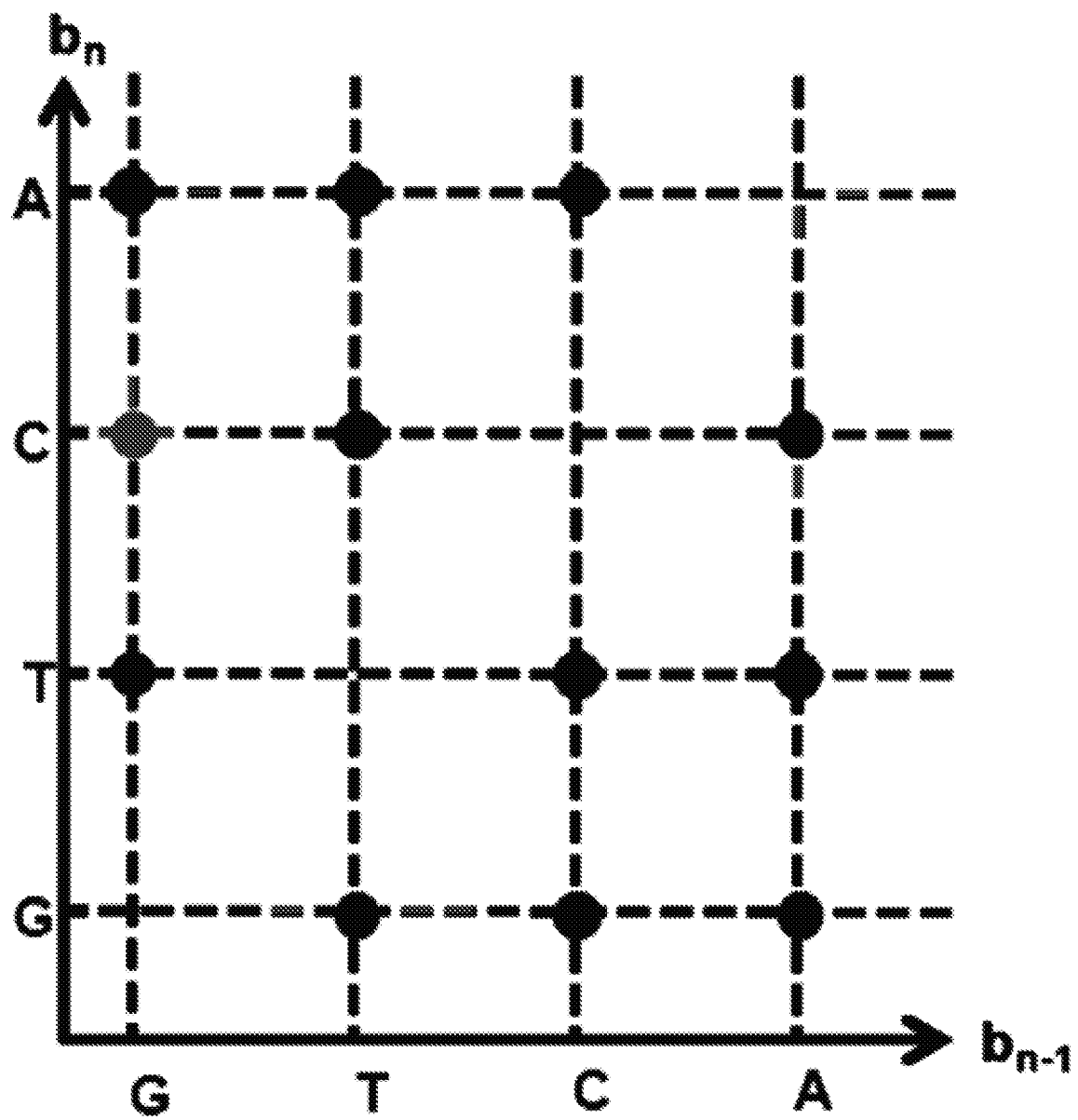
FIG. 4 shows a diagram of a constellation mapping in accordance with various aspects of this disclosure.

FIG. 4 shows a diagram of a mapping 400 (e.g., signal constellation mapping, signal constellation diagram, etc.) in accordance with various aspects of this disclosure. The mapping 400 may be associated with a multi-dimensional mapping of DNA sequences, in accordance with various examples. Mapping 400 may be generated by mapping module 205 of FIG. 2.

In some cases, homopolymers (i.e., runs of 2 or more identical DNA bases) may be associated with higher error rates in DNA storage. In some cases, the number of bits stored per base may be maximized in absence of homopolymers. Eliminating homopolymers results in three options per base (e.g., AC, AT, or AG for Adenine, CA, CT, or CG for Cytosine, etc.). In some cases, the theoretical limit for bits/base may be equal to $\log_2(3)=1.585$. In one embodiment, DNA mapping module 130 may eliminate homopolymers between DNA bases $b_{n-1}$ and $b_n$. As depicted, mapping 400 may depict a mapping where homopolymers between DNA bases $b_{n-1}$ and $b_n$ are eliminated (e.g., elimination of AA, CC, TT, and GG).

In one embodiment, mapping 400 may depict consecutive base values $b_{n-1}$ and $b_n$ at time "n−1" and "n." Mapping 400 depicts all of the 12 possible combinations between $b_{n-1}$ and $b_n$ excluding homopolymers. In some embodiments, based on the possible value of $b_{n-2}$ before $b_{n-1}$ one of the columns in mapping 400 (e.g., three combinations) may also eliminated to exclude the potential existence of a homopolymer between time n−2 and n−1, resulting in 9 possible combinations at a given time. In one embodiment, mapping 400 may be based at least in part on the stipulation that the value of $b_{n-2}$ eliminates one of the columns in mapping 400. In one embodiment, mapping 400 may be based at least in part on a stipulation that among the remaining 9 possible combinations, one of the combination may be removed that reduce the number of neighbors of each combination in mapping 400, resulting in an optimization of both the system SNR and BER. In one embodiment, mapping 400 may be based at least in part on assigning $2^3=8$ 3-bit combinations to each 8 $(b_{n-1}, b_n)$ pairs such that all or most 3-bit combinations have only 1 bit difference between adjacent $(b_{n-1}, b_n)$ pairs, resulting in an optimization of the system BER.

Figure 5:
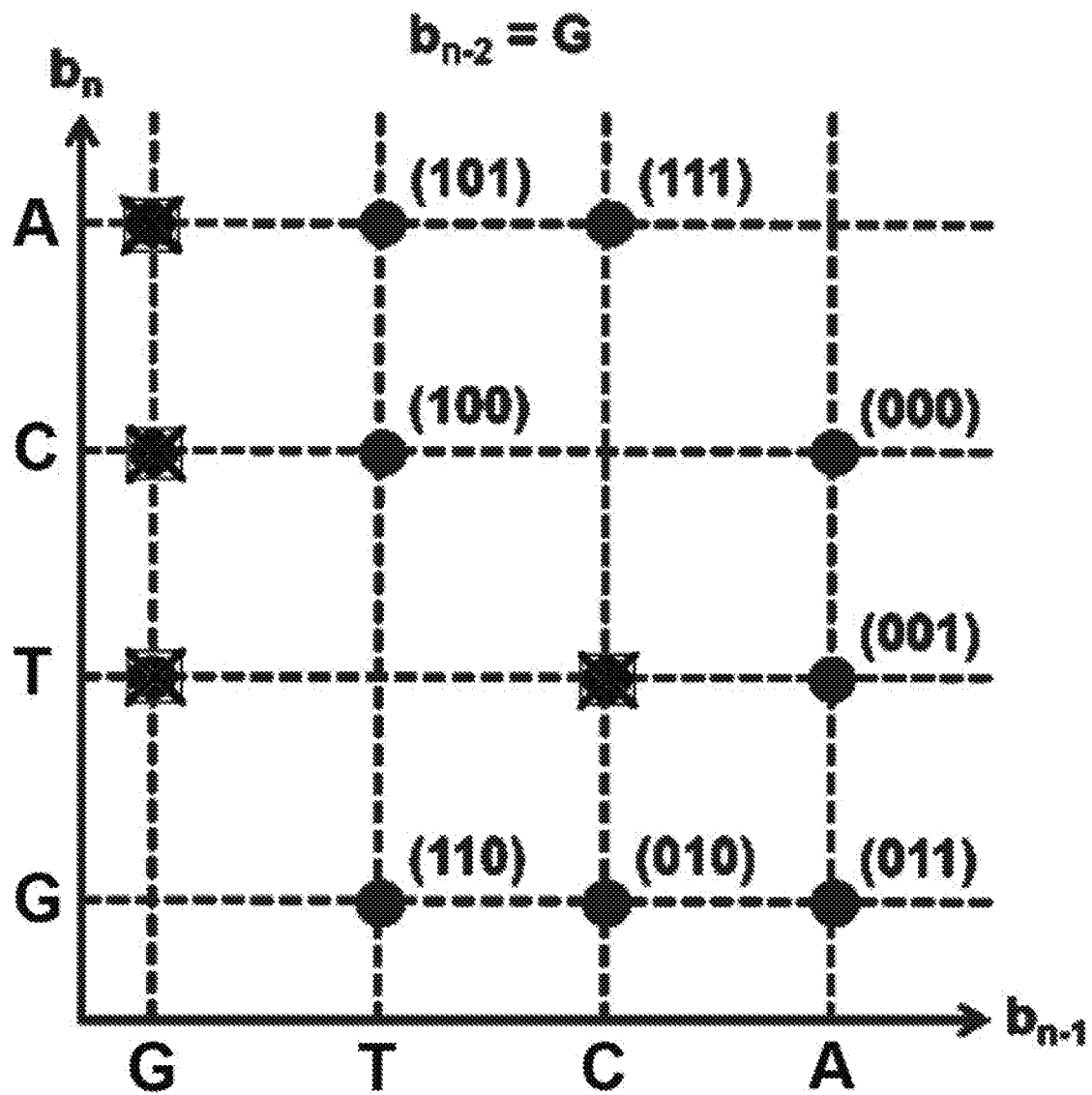
FIG. 5 shows a diagram of a constellation mapping in accordance with various aspects of this disclosure.

FIG. 5 shows a diagram of a mapping 500 in accordance with various aspects of this disclosure. The mapping 500 may be associated with a multi-dimensional mapping of DNA sequences, in accordance with various examples. Mapping 500 may be generated by mapping module 205 of FIG. 2.

As depicted in mapping 500, when $b_{n-2}=G$, DNA mapping module 130 may eliminate combinations in mapping 400 of FIG. 4 with $b_{n-1}=G$ to eliminate homopolymers in the DNA encoding, leaving 9 possible combinations. In one embodiment, among the remaining 9 combinations, timing recovery module 130 may eliminate $(b_{n-1}, b_n)=(C, T)$ when $b_{n-2}=G$, reducing the maximum number of node neighbors for each node to two neighbors. For instance, before eliminating $(b_{n-1}, b_n)=(C, T)$, $(b_{n-1}, b_n)=(A, T)$ included three node neighbors: $(b_{n-1}, b_n)=(A, C)$, $(b_{n-1}, b_n)=(A, G)$, and $(b_{n-1}, b_n)=(C, T)$. With $(b_{n-1}, b_n)=(C, T)$ eliminated, $(b_{n-1}, b_n)=(A, T)$ is left with a maximum of two node neighbors: $(b_{n-1}, b_n)=(A, C)$ and $(b_{n-1}, b_n)=(A, G)$. In some cases, timing recovery module 130 may assign 3-bit combinations to the remaining 8 pairs $(b_{n-1}, b_n)$ as follows, resulting in a maximum 1-bit difference between the remaining neighboring pairs $(b_{n-1}, b_n)$:

$(b_{n-1}, b_n)=(A, C)$ maps to 000
$(b_{n-1}, b_n)=(A, T)$ maps to 001
$(b_{n-1}, b_n)=(A, G)$ maps to 011
$(b_{n-1}, b_n)=(C, G)$ maps to 010
$(b_{n-1}, b_n)=(T, G)$ maps to 110
$(b_{n-1}, b_n)=(T, C)$ maps to 100
$(b_{n-1}, b_n)=(T, A)$ maps to 101
$(b_{n-1}, b_n)=(C, A)$ maps to 111

Figure 6:
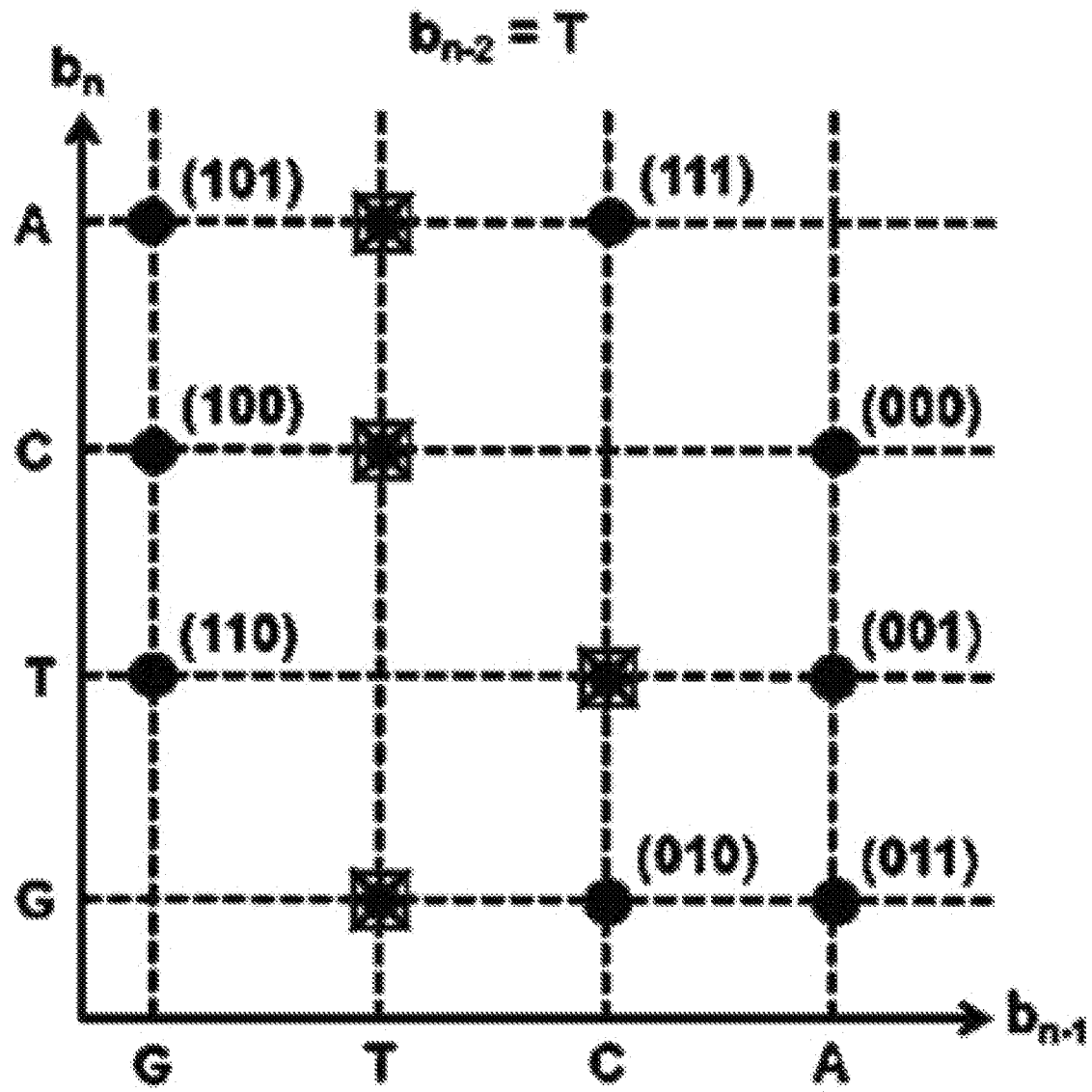
FIG. 6 shows a diagram of a constellation mapping in accordance with various aspects of this disclosure.

FIG. 6 shows a diagram of a mapping 600 in accordance with various aspects of this disclosure. The mapping 600 may be associated with a multi-dimensional mapping of DNA sequences, in accordance with various examples. Mapping 600 may be generated by mapping module 205 of FIG. 2.

As depicted in mapping 600, when $b_{n-2}=T$, DNA mapping module 130 may eliminate combinations in mapping 400 of FIG. 4 with $b_{n-1}=T$, leaving 9 possible combinations. Among the remaining 9 combinations, DNA mapping module 130 may eliminate $(b_{n-1}, b_n)=(C, T)$, reducing the maximum number of neighbors for each node to two. In some cases, DNA mapping module 130 may assign the 3-bit combinations to the remaining 8 pairs $(b_{n-1}, b_n)$ as follows, resulting in a maximum 1-bit difference between the neighboring pairs $(b_{n-1}, b_n)$:

$(b_{n-1}, b_n)=(A, C)$ maps to 000
$(b_{n-1}, b_n)=(A, T)$ maps to 001
$(b_{n-1}, b_n)=(A, G)$ maps to 011
$(b_{n-1}, b_n)=(C, G)$ maps to 010
$(b_{n-1}, b_n)=(G, T)$ maps to 110
$(b_{n-1}, b_n)=(G, C)$ maps to 100
$(b_{n-1}, b_n)=(G, A)$ maps to 101
$(b_{n-1}, b_n)=(C, A)$ maps to 111

Figure 7:
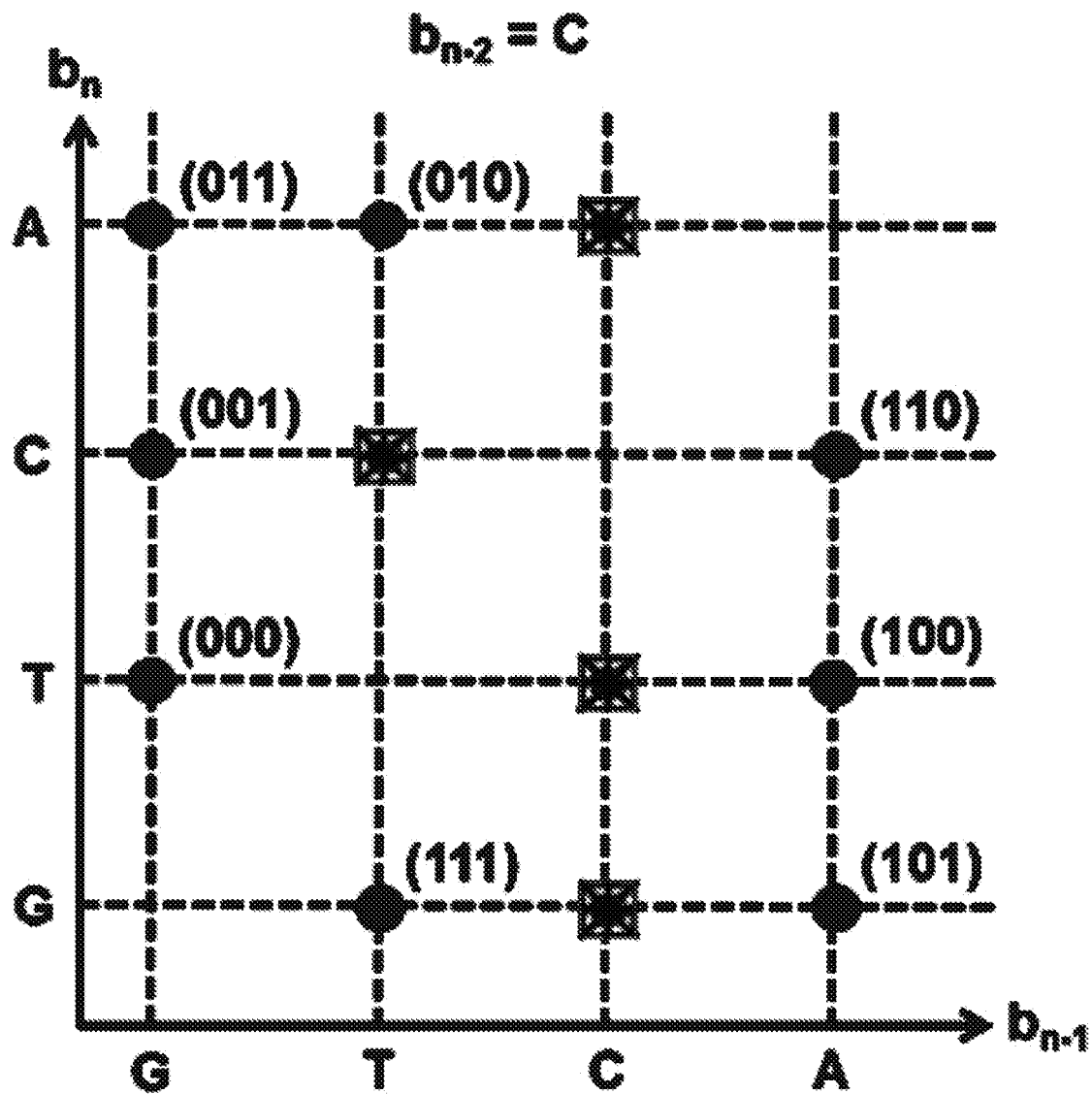
FIG. 7 shows a diagram of a constellation mapping in accordance with various aspects of this disclosure.

FIG. 7 shows a diagram of a mapping 700 in accordance with various aspects of this disclosure. The mapping 700 may be associated with a multi-dimensional mapping of DNA sequences, in accordance with various examples. Mapping 700 may be generated by mapping module 205 of FIG. 2.

As depicted in mapping 700, when $b_{n-2}=C$, DNA mapping module 130 may eliminate combinations in mapping 400 of FIG. 4 with $b_{n-1}=C$, leaving 9 possible combinations. Among the remaining 9 combinations, DNA mapping module 130 may eliminate $(b_{n-1}, b_n)=(T, C)$, reducing the maximum number of neighbors for each node to two. In some cases, DNA mapping module 130 may assign the 3-bit combinations to the remaining 8 $(b_{n-1}, b_n)$ as follows, resulting in a maximum 1-bit difference between the neighboring pairs $(b_{n-1}, b_n)$:

$(b_{n-1}, b_n)=(A, C)$ maps to 110
$(b_{n-1}, b_n)=(A, T)$ maps to 100
$(b_{n-1}, b_n)=(A, G)$ maps to 101
$(b_{n-1}, b_n)=(T, G)$ maps to 111
$(b_{n-1}, b_n)=(G, T)$ maps to 000
$(b_{n-1}, b_n)=(G, C)$ maps to 001
$(b_{n-1}, b_n)=(G, A)$ maps to 011
$(b_{n-1}, b_n)=(T, A)$ maps to 010

Figure 8:
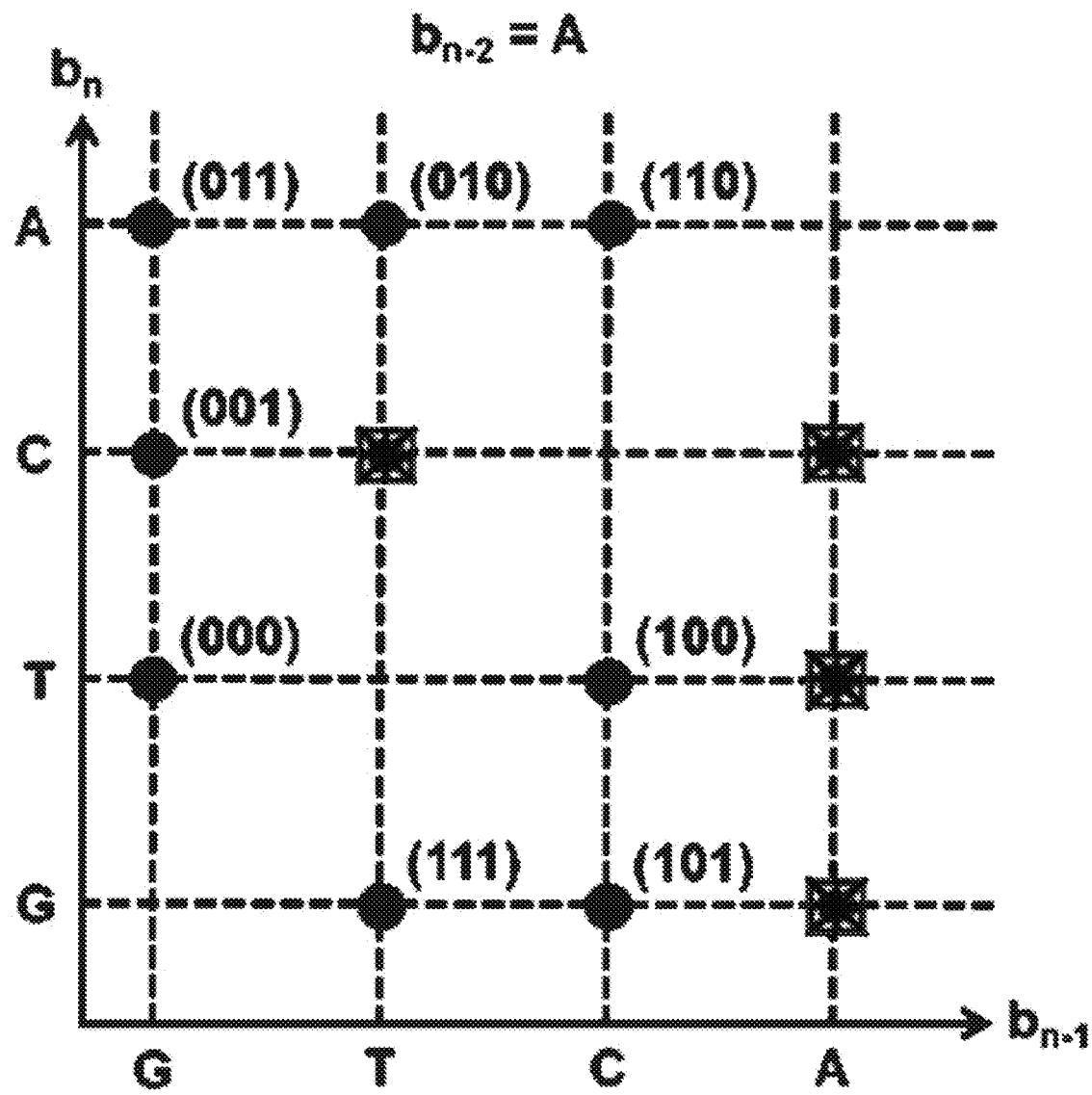
FIG. 8 shows a diagram of a constellation mapping in accordance with various aspects of this disclosure.

FIG. 8 shows a diagram of a mapping 800 in accordance with various aspects of this disclosure. The mapping 800 may be associated with a multi-dimensional mapping of DNA sequences, in accordance with various examples. Mapping 800 may be generated by mapping module 205 of FIG. 2.

As depicted in mapping 800, when $b_{n-2}=A$, DNA mapping module 130 may eliminate combinations in mapping 400 of FIG. 4 with $b_{n-1}=A$, leaving 9 possible combinations. Among the remaining 9 combinations, eliminate $(b_{n-1}, b_n)=(T, C)$, reducing the maximum number of neighbors for each node to two. In some cases, DNA mapping module 130 may assign the 3-bit combinations to the remaining 8 pairs $(b_{n-1}, b_n)$ as follows, resulting in a maximum 1-bit difference between the neighboring pairs $(b_{n-1}, b_n)$:

$(b_{n-1}, b_n)=(C, A)$ maps to 110
$(b_{n-1}, b_n)=(C, T)$ maps to 100
$(b_{n-1}, b_n)=(C, G)$ maps to 101
$(b_{n-1}, b_n)=(T, G)$ maps to 111
$(b_{n-1}, b_n)=(G, T)$ maps to 000
$(b_{n-1}, b_n)=(G, C)$ maps to 001
$(b_{n-1}, b_n)=(G, A)$ maps to 011
$(b_{n-1}, b_n)=(T, A)$ maps to 010

As shown in the mappings of FIGS. 5-8, DNA mapping module 130 may map 3 binary bits to 2 DNA bases, resulting in a bits/base ratio of 1.5, which approaches the theoretical limit of 1.585. As also shown in the mappings of FIGS. 5-8, DNA mapping module 130 optimizes system SNR and BER. As also shown in the mappings of FIGS. 5-8, DNA mapping module 130 works with any data bit combinations, independent of whether the data is compressed or uncompressed, and/or whether the data is encoded or decoded.

The bit/base ratio may be further improved towards its theoretical limit by increasing the length of consecutive base values. For example, DNA mapping module 130 may generate mappings based on 7 consecutive base values (e.g., $b_{n-6}, b_{n-5}, b_{n-4}, b_{n-3}, b_{n-2}, b_{n-1}, b_n$), instead of the exemplary 2 consecutive base values from FIGS. 5-8. Using 7 consecutive base values may provide $3^7=2,187$ possible combinations $(b_{n-6}, b_{n-5}, b_{n-4}, b_{n-3}, b_{n-2}, b_{n-1}, b_n)$ and enables DNA mapping module 130 to map $2^{11}=2,048$ 11-bit combinations. In one embodiment, DNA mapping module 130 may eliminate the remaining 2,187−2,048=139 combinations to optimize the system SNR and BER. Accordingly, the bits/base ratio becomes 11/7=~1.57, which is within 0.0135 to the theoretical limit of 1.585.

Figure 9:
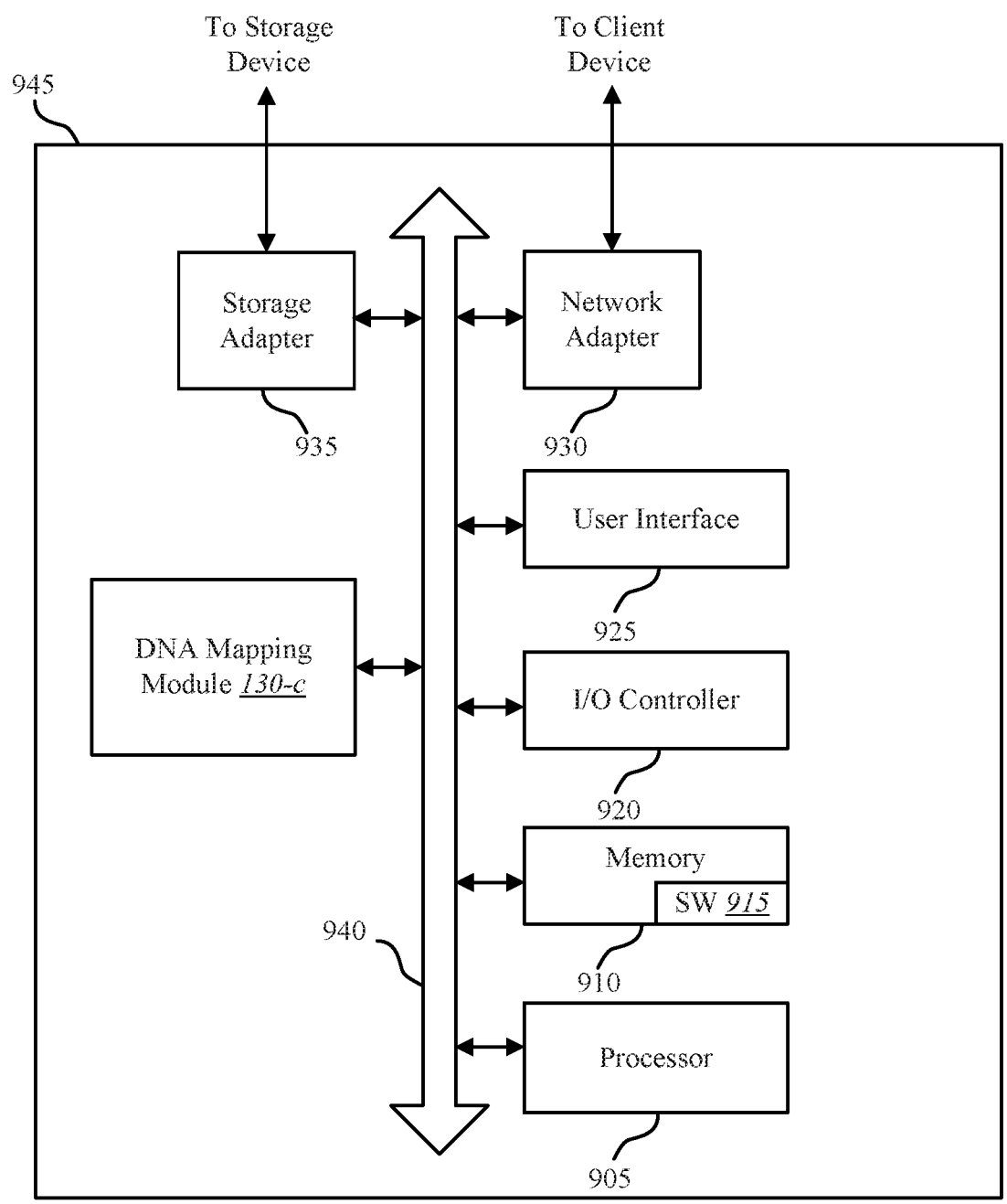
FIG. 9 shows one embodiment of a system in accordance with various aspects of this disclosure.

FIG. 9 shows a system 900 for multi-dimensional mapping of DNA sequences, in accordance with various examples. System 900 may include an apparatus 945, which may be an example of any one of device 105 of FIG. 1.

Apparatus 945 may include components for bi-directional voice and data communications including components for transmitting communications and components for receiving communications. For example, apparatus 945 may communicate bi-directionally with one or more storage devices (e.g., DNA storage devices) and/or client systems. This bi-directional communication may be direct (apparatus 945 communicating directly with a storage system, for example) and/or indirect (apparatus 945 communicating indirectly with a storage device or client device through a server, for example).

Apparatus 945 may also include a processor module 905, and memory 910 (including software/firmware code (SW) 915), an input/output controller module 920, a user interface module 925, a network adapter 930, and a storage adapter 935. Apparatus 945 may include one or more processors. The software/firmware code 915 may be one example of a software application executing on apparatus 945. The network adapter 930 may communicate bi-directionally, via one or more wired links and/or wireless links, with one or more networks and/or client devices. In some embodiments, network adapter 930 may provide a direct connection to a client device via a direct network link to the Internet via a POP (point of presence). In some embodiments, network adapter 930 of apparatus 945 may provide a connection using wireless techniques, including digital cellular telephone connection, Cellular Digital Packet Data (CDPD) connection, digital satellite data connection, and/or another connection. The apparatus 945 may include DNA mapping module 130-c, which may perform the functions described above for the DNA mapping module 130 of FIGS. 1 and/or 2.

The signals associated with system 900 may include wireless communication signals such as radio frequency, electromagnetics, local area network (LAN), wide area network (WAN), virtual private network (VPN), wireless network (using 802.11, for example), cellular network (using 3G and/or LTE, for example), and/or other signals. The network adapter 930 may enable one or more of WWAN (GSM, CDMA, and WCDMA), WLAN (including BLUETOOTH® and Wi-Fi), WMAN (WiMAX) for mobile communications, antennas for Wireless Personal Area Network (WPAN) applications (including RFID and UWB), or any combination thereof.

One or more buses 940 may allow data communication between one or more elements of apparatus 945 such as processor module 905, memory 910, I/O controller module 920, user interface module 925, network adapter 930, and storage adapter 935, or any combination thereof. One or more of the components of the apparatus 945, individually or collectively, may be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used such as Structured/Platform ASICs, Field Programmable Gate Arrays (FPGAs), and other Semi-Custom ICs, which may be programmed in any manner known in the art. The functions of each module may also be implemented, in whole or in part, with instructions embodied in memory formatted to be executed by one or more general and/or application-specific processors.

The memory 910 may include random access memory (RAM), read only memory (ROM), flash memory, and/or other types. The memory 910 may store computer-readable, computer-executable software/firmware code 915 including instructions that, when executed, cause the processor module 905 to perform various functions described in this disclosure. Alternatively, the software/firmware code 915 may not be directly executable by the processor module 905 but may cause a computer (when compiled and executed, for example) to perform functions described herein. Alternatively, the computer-readable, computer-executable software/firmware code 915 may not be directly executable by the processor module 905, but may be configured to cause a computer, when compiled and executed, to perform functions described herein. The processor module 905 may include an intelligent hardware device, for example, a central processing unit (CPU), a microcontroller, an application-specific integrated circuit (ASIC), field programmable gate array (FPGA), or any combination thereof.

In some embodiments, the memory 910 may contain, among other things, the Basic Input-Output system (BIOS) which may control basic hardware and/or software operation such as the interaction with peripheral components or devices. For example, at least a portion of the DNA mapping module 130-c to implement the present techniques may be stored within the system memory 910. Applications resident with system 900 are generally stored on and accessed via a non-transitory computer readable medium, such as a hard disk drive or other storage medium. Additionally, applications can be in the form of electronic signals modulated in accordance with the application and data communication technology when accessed via a network interface such as network adapter 930.

Many other devices and/or subsystems may be connected to and/or included as one or more elements of system 900 (for example, a personal computing device, mobile computing device, smart phone, server, internet-connected device, cell radio module, or any combination thereof). In some embodiments, all of the elements shown in FIG. 9 need not be present to practice the present techniques. The devices and subsystems can be interconnected in different ways from that shown in FIG. 9. In some embodiments, an aspect of some operation of a system, such as that shown in FIG. 9, may be readily known in the art and are not discussed in detail in this application. Code to implement the present disclosure can be stored in a non-transitory computer-readable medium such as one or more of system memory 910 or other memory. The operating system provided on I/O controller module 920 may be a mobile device operation system, a desktop/laptop operating system, a server operating system, or another known operating system.

The I/O controller module 920 may operate in conjunction with network adapter 930 and/or storage adapter 935. The network adapter 930 may enable apparatus 945 with the ability to communicate with client devices such as device 105 of FIG. 1, and/or other devices over a communication network. Network adapter 930 may provide wired and/or wireless network connections. In some cases, network adapter 930 may include an Ethernet adapter or Fibre Channel adapter. Storage adapter 935 may enable apparatus 945 to access one or more data storage devices such as storage device 110. The one or more data storage devices may include two or more data tiers each. The storage adapter 935 may include one or more of an Ethernet adapter, a Fibre Channel adapter, Fibre Channel Protocol (FCP) adapter, a SCSI adapter, and iSCSI protocol adapter.

Figure 10:
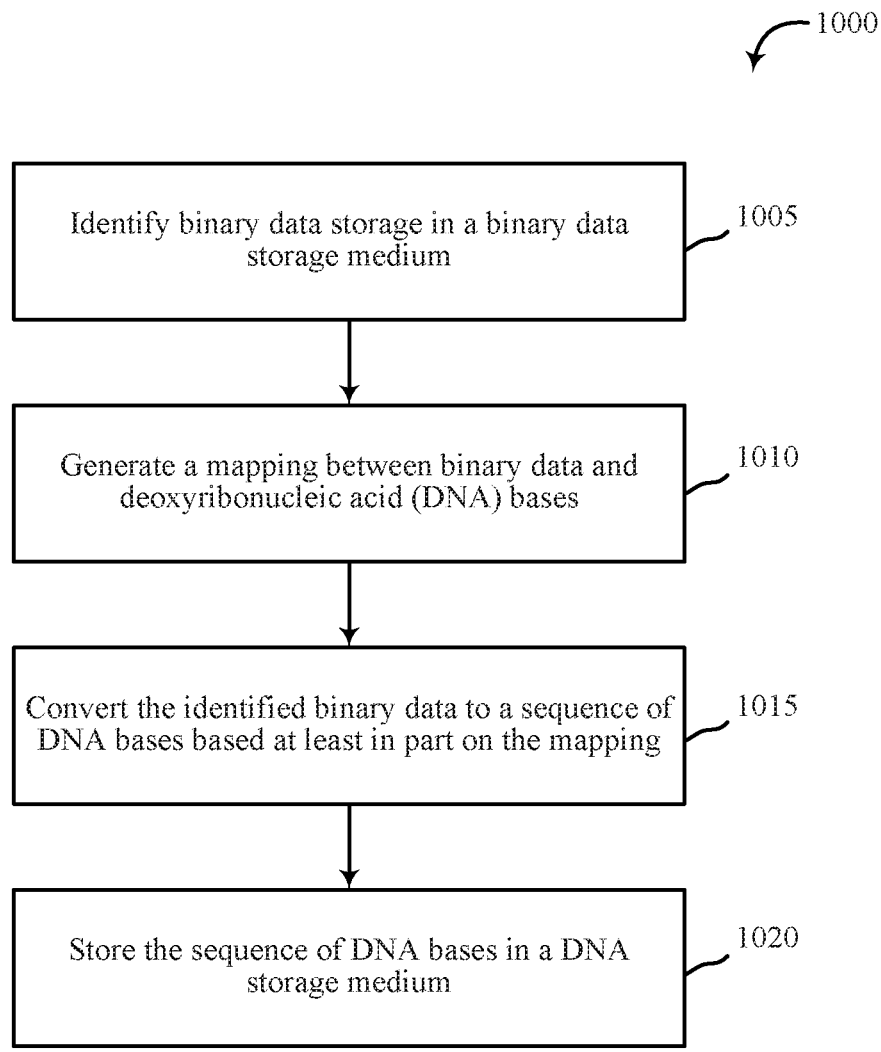
FIG. 10 is a flow chart illustrating an example of a method in accordance with various aspects of this disclosure.

FIG. 10 is a flow chart illustrating an example of a method 1000 for multi-dimensional mapping of DNA sequences, in accordance with various aspects of the present disclosure. One or more aspects of the method 1000 may be implemented in conjunction with device 105 of FIG. 1, apparatus 945 of FIG. 9, and/or DNA mapping module 130 depicted in FIGS. 1, 2 and/or 9. In some examples, a backend server, computing device, and/or storage device may execute one or more sets of codes to control the functional elements of the backend server, computing device, and/or storage device to perform one or more of the functions described below. Additionally or alternatively, the backend server, computing device, and/or storage device may perform one or more of the functions described below using special-purpose hardware.

At block 1005, the method 1000 may include identifying binary data storage in a binary data storage medium. At block 1010, the method 1000 may include generating a mapping between binary data and deoxyribonucleic acid (DNA) bases. At block 1015, the method 1000 may include converting the identified binary data to a sequence of DNA bases based at least in part on the mapping. At block 1020, the method 1000 may include storing the sequence of DNA bases in a DNA storage medium.

The operation(s) at block 1005-1020 may be performed using the DNA mapping module 130 described with reference to FIGS. 1, 2, and 9, and/or another module described herein. Thus, the method 1000 may provide for multi-dimensional mapping of binary data DNA sequences. It should be noted that the method 1000 is just one implementation and that the operations of the method 1000 may be rearranged, omitted, and/or otherwise modified such that other implementations are possible and contemplated.

Figure 11:
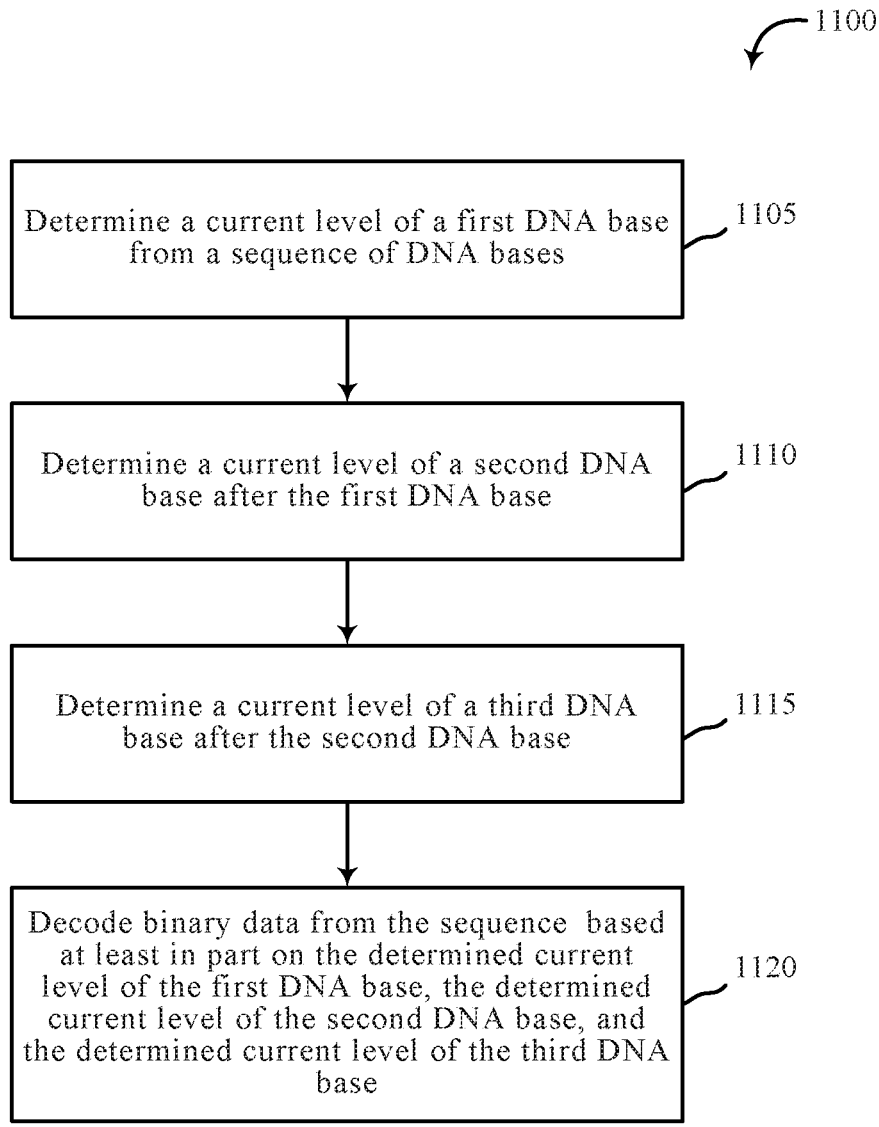
FIG. 11 is a flow chart illustrating an example of a method in accordance with various aspects of this disclosure.

FIG. 11 is a flow chart illustrating an example of a method 1100 for multi-dimensional mapping of DNA sequences, in accordance with various aspects of the present disclosure. One or more aspects of the method 1100 may be implemented in conjunction with device 105 of FIG. 1, apparatus 945 of FIG. 9, and/or DNA mapping module 130 depicted in FIGS. 1, 2 and/or 9. In some examples, a backend server, computing device, and/or storage device may execute one or more sets of codes to control the functional elements of the backend server, computing device, and/or storage device to perform one or more of the functions described below. Additionally or alternatively, the backend server, computing device, and/or storage device may perform one or more of the functions described below using special-purpose hardware.

At block 1105, the method 1100 may include determining a current level of a first DNA base from a sequence of DNA bases. At block 1110, the method 1100 may include determining a current level of a second DNA base after the first DNA base. At block 1115, the method 1100 may include determining a current level of a third DNA base after the second DNA base. At block 1120, the method 1100 may include decoding binary data from the sequence based at least in part on the determined current level of the first DNA base, the determined current level of the second DNA base, and the determined current level of the third DNA base.

The operation(s) at block 1105-1120 may be performed using the DNA mapping module 130 described with reference to FIGS. 1, 2, and 9, and/or another module described herein. Thus, the method 1100 may provide for multi-dimensional mapping of binary data DNA sequences. It should be noted that the method 1100 is just one implementation and that the operations of the method 1100 may be rearranged, omitted, and/or otherwise modified such that other implementations are possible and contemplated.

In some examples, aspects from two or more of the methods 1000 and 1100 may be combined and/or separated. It should be noted that the methods 1000 and 1100 are just example implementations, and that the operations of methods 1000 and 1100 may be rearranged or otherwise modified such that other implementations are possible.

Figure 12:
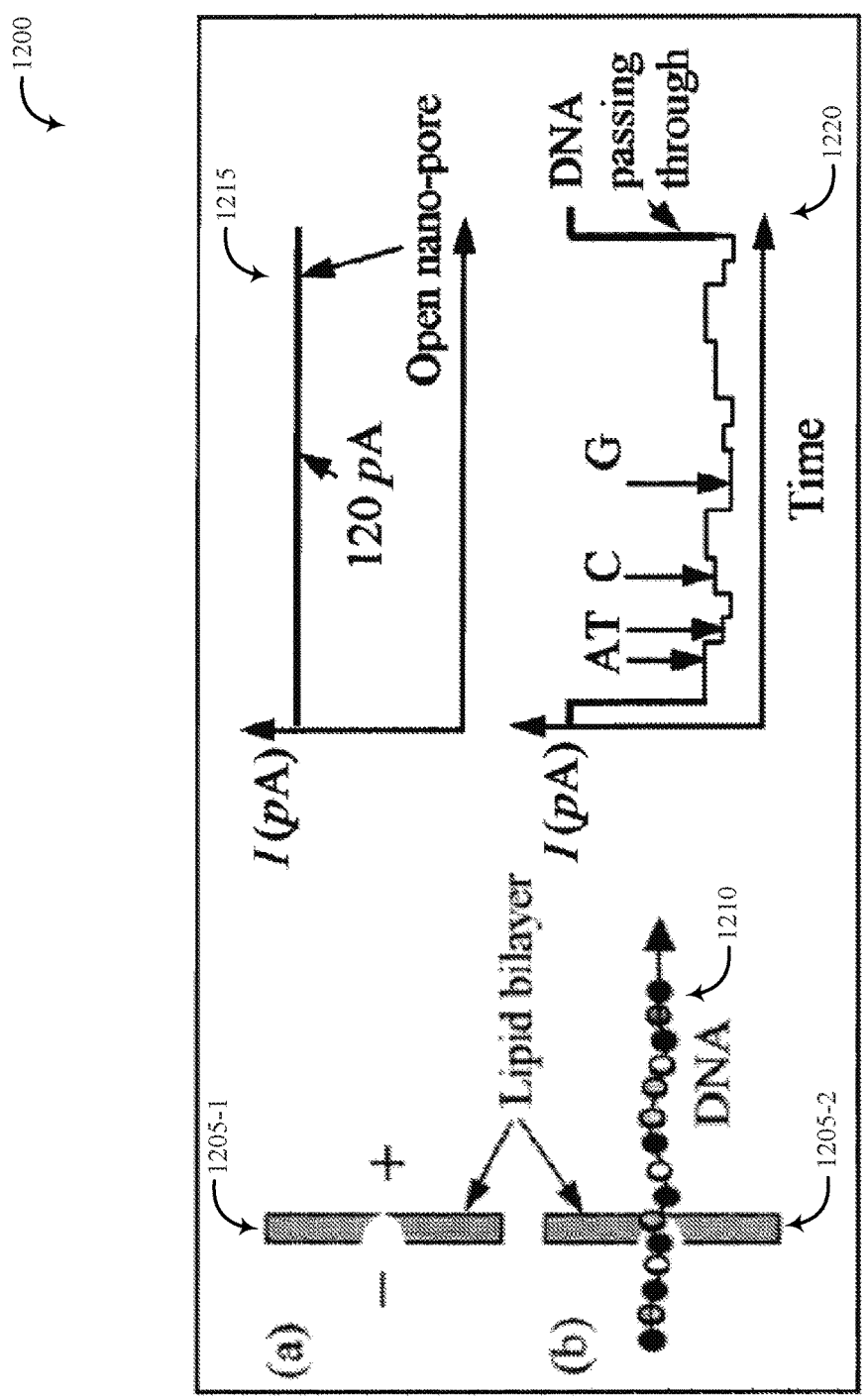
FIG. 12 is a diagram of a DNA reading system in accordance with various aspects of this disclosure.

FIG. 12 is a diagram of a DNA reading system 1200 in accordance with various aspects of this disclosure. As shown, DNA reading system 1200 may include a nano-pore (e.g., nano-pore 1205-1 and nano-pore 1205-2). As shown, nano-pore 1205-1 depicts an open nano-pore created in a lipid membrane by alpha-hemolysin proteins, where the bilayer separates two sections (−,+) of a buffer solution. With a voltage applied across the bilayer, a current may flow through the nano-pore 1205-1. For example, as depicted in current chart 1215, with 100 millivolts (mV) applied across the bilayer, a current of approximately 120 picoamps (pA) may flow across the bilayer.

As shown, DNA reading system 1200 may include a strand of DNA (e.g., DNA strand 1210). As depicted, the DNA strand 1210 may be passed through nano-pore 1205-2. In one embodiment, DNA reading system 1200 detects each nucleotide (i.e., DNA base) in a strand of DNA bases (e.g., DNA strand 1210) as the strand passes through a nano-pore. As shown, as different nucleotides pass through nano-pore 1205-2, each nucleotide of DNA strand 1210 affects the flow of the ionic current differently. For example, an adenine nucleotide passing through nano-pore 1205-2 may affect the flow of the ionic current differently than a guanine nucleotide passing through nano-pore 1205-2, as depicted in current chart 1220, where fluctuations in current blockage may be due to differences in the size and/or charge of the various nucleotides passing through the nano-pore (e.g., different current readings for adenine (A), thymine (T), cytosine (C), and guanine (G), etc.). In some embodiments, DNA reading system 1200 uniquely identifies each nucleotide by analyzing the electrolytic current waveform associated with each base as it passes through the nano-pore. In some cases, DNA mapping module 130, in conjunction with one or more processors, may detect the variations in the flow of the ionic current to identify each nucleotide as is passes through nano-pore 1205-2.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, for example, a combination of a DSP and a microprocessor, multiple microprocessors, one or more microprocessors in conjunction with a DSP core, and/or any combination thereof.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC, or A and B and C.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, or any combination thereof, then the coaxial cable, fiber optic cable, twisted pair, DSL, or wireless technologies such as infrared, radio, and/or microwave are included in the definition of medium. Disk and disc, as used herein, include any combination of compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein but is accorded the broadest scope consistent with the principles and novel features disclosed.

This disclosure may specifically apply to security system applications. This disclosure may specifically apply to storage system applications. In some embodiments, the concepts, the technical descriptions, the features, the methods, the ideas, and/or the descriptions may specifically apply to storage and/or data security system applications. Distinct advantages of such systems for these specific applications are apparent from this disclosure.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present techniques to the precise forms discussed. Many modifications and variations are possible in view of the above teachings. The embodiments were chosen and described in order to explain the principles of the present techniques and their practical applications, to enable others skilled in the art to utilize the present systems, apparatus, and methods and various embodiments with various modifications as may be suited to the particular use contemplated.

What is claimed is:

1. A deoxyribonucleic acid (DNA) data storage system comprising:
   a DNA reader for reading sequences of DNA bases formed without homopolymers in adjacent pairs of DNA bases, the DNA reader configured to measure respective current levels indicative of respective DNA bases from a sequence of DNA bases, based, at least in part, on a read process performed on the sequence of DNA bases, and to output a sequence of current levels of such determined respective current levels as current level data;
   a memory storing processor-implementable instructions, and further storing a signal constellation diagram including a plurality of nodes that multi-dimensionally represent a digital bit to DNA base ratio approaching a theoretical limit of 1.585, wherein each node corresponds to a fixed-length, particular ordered set of adjacent DNA base types and an associated multi-digit, binary number combination; and
   a processor configured to decode binary data from the current level data by instantiation of the processor-implementable instructions which instruct the processor to:
      receive the current level data from the DNA reader;
      associate respective DNA base types corresponding to each respective measured current level in the sequence of current levels;
      map sets of adjacent DNA base types determined in the sequence of current levels to corresponding nodes of the signal constellation diagram; and
      construct decoded binary data from the multi-digit, binary number combinations associated with each node of the signal constellation diagram, with a maximum of one bit difference between the multi-digit, binary number combinations in any adjacent node, thereby optimizing a bit error rate of the decoded binary data and a signal to noise ratio of the current level data; and
   a storage device in communication with the processor that receives and stores the decoded binary data.

2. The DNA data storage system of claim 1, wherein:
   each ordered set of adjacent DNA base types is one of nine possible ordered combinations of adjacent DNA base types; and
   each of the nine possible ordered combinations of adjacent DNA base types respectively maps to a respective node of the signal constellation diagram.

3. The DNA data storage system of claim 1, wherein the processor is further configured to map each ordered set of adjacent DNA base types on a selected one of multiple different configurations of arrays of nodes within the signal constellation diagram based upon which DNA base type is positioned immediately before a respective ordered set of adjacent DNA base types.

4. The DNA data storage system of claim 1, wherein:
   the particular ordered set of adjacent DNA base types includes eight possible combinations of adjacent pairs of DNA base types;
   each of the eight possible combinations of adjacent pairs of DNA base types respectively maps to a respective node of the signal constellation diagram; and
   the processor is further configured to provide that each of eight nodes of the signal constellation diagram mapped by the adjacent pairs of DNA base types has a maximum of two mapped node neighbors.

5. The DNA data storage system of claim 4, wherein the processor is further configured to map each of the eight possible combinations of adjacent pairs of DNA base types to one of eight 3-bit binary values, respectively.

6. The DNA data storage system of claim 1, wherein the read process is based at least in part on detecting changes in ionic current while passing the sequence through a nano-pore of the DNA reader, a different current output occurring for each DNA base of the sequence of DNA bases passed through the nano-pore, each DNA base of the sequence of DNA bases being one of Adenine, Guanine, Cytosine, or Thymine.

7. The DNA data storage system of claim 1, wherein the signal constellation diagram is configured in three dimensions or greater.

8. The DNA data storage system of claim 1, wherein for a signal constellation diagram formed of possible base pairs of a first DNA base type and a second DNA base type:
   the processor is configured to eliminate one or more nodes from the signal constellation diagram as mappable nodes; and
   the eliminated nodes correspond to possible combinations between the possible base pairs of the first DNA base type and the second DNA base type in which the possible base types of the second DNA base type are equivalent DNA base types to a third DNA base type following the second DNA base type.

9. The DNA data storage system of claim 8, wherein:
   the processor is further configured to select and eliminate a further node from the signal constellation diagram as a mappable node; and
   the further node is selected such that respective bit combinations in each remaining mappable node in the signal constellation diagram have only a single-bit difference from each bit combination in each adjacent node to reduce bit error rate.

10. The DNA data storage system of claim 8, wherein a location of the first DNA base type occurs corresponding to a start of the sequence of DNA bases or after the start of the sequence of DNA bases.

11. A deoxyribonucleic acid (DNA) reader apparatus configured to:
   measure respective current levels indicative of respective DNA bases from a sequence of DNA bases formed without homopolymers in adjacent pairs of DNA bases, based at least in part on a read process performed on the sequence of DNA bases; and
   decode binary data from the sequence of DNA bases from the respective current levels by:
      associating respective DNA base types with respective measured current levels from the read process performed on the sequence of DNA bases; and
      mapping sets of adjacent DNA base types to corresponding nodes of a signal constellation diagram, wherein the signal constellation diagram includes a plurality of nodes that multi-dimensionally represent a digital bit to DNA base ratio approaching a theoretical limit of 1.585, and
         each node corresponds to a fixed-length, particular ordered set of adjacent DNA base types and an associated multi-digit, binary number combination; and
      constructing decoded binary data from the unique, multi-digit, binary number combinations associated with each node of the signal constellation diagram, with a maximum of one bit difference between the unique, multi-digit, binary number combinations in any adjacent node, thereby optimizing a bit error rate of the decoded binary data and a signal to noise ratio of the measured current levels.

12. The apparatus of claim 11, wherein:
each ordered set of adjacent pairs of DNA base types is one of nine possible ordered combinations of adjacent DNA base types; and
each of the nine possible ordered combinations of adjacent DNA base types respectively maps to a respective node of the signal constellation diagram.

13. The apparatus of claim 11 further configured to map each ordered set of adjacent DNA base types on a selected one of multiple different configurations of arrays of nodes within the signal constellation diagram based upon which DNA base is positioned immediately before a respective ordered set of adjacent DNA base types.

14. The apparatus of claim 11, wherein:
the particular ordered set of adjacent DNA base types includes eight possible combinations of adjacent pairs of DNA base types;
each of the eight possible combinations of adjacent pairs of DNA base types respectively maps to a respective node of the signal constellation diagram; and
the apparatus is further configured to provide that each of eight nodes of the signal constellation diagram mapped by the adjacent pairs of DNA base types has a maximum of two mapped node neighbors.

15. The apparatus of claim 14, wherein the apparatus is further configured to map each of the eight possible combinations of adjacent pairs of DNA bases to one of eight 3-bit binary values, respectively.

16. The apparatus of claim 11, wherein for a signal constellation diagram formed of possible base pairs of a first DNA base type and a second DNA base type:
the apparatus is configured to eliminate one or more nodes from the signal constellation diagram as mappable nodes; and
the eliminated nodes correspond to possible combinations between the possible base pairs of the first DNA base type and the second DNA base type in which the possible base types of the second DNA base type are equivalent DNA base types to a third DNA base type following the second DNA base type.

17. The apparatus of claim 16, wherein:
the apparatus is further configured to select and eliminate a further node from the signal constellation diagram as a mappable node; and
the further node is selected such that respective bit combinations in each remaining mappable node in the signal constellation diagram has only a single-bit difference from each bit combination in each adjacent node to reduce bit error rate.

18. The apparatus of claim 16, wherein a location of the first DNA base type occurs corresponding to the start of the sequence of DNA bases or after the start of the sequence of DNA bases.

19. A method implemented by a combination of a deoxyribonucleic acid (DNA) reader and a computer processor comprising:
measuring respective current levels indicative of respective DNA bases from a sequence of DNA bases formed without homopolymers in adjacent pairs of DNA bases, based at least in part on a read process performed on the sequence of DNA bases by the DNA reader, wherein the read process is based at least in part on detecting changes in ionic current while passing the respective DNA bases through a nano-pore in the DNA reader; and
decoding, using the computer processor, binary data from the sequence of DNA bases from the respective current levels by;
associating respective DNA base types with respective measured current levels from the read process performed on the sequence of DNA bases; and
mapping sets of adjacent DNA base types to corresponding nodes of a signal constellation diagram, wherein
the signal constellation diagram includes a plurality of nodes that multi-dimensionally represent a digital bit to DNA base ratio approaching a theoretical limit of 1.585, and
each node corresponds to a fixed-length, particular ordered set of adjacent DNA base types and an associated multi-digit, binary number combination; and
constructing decoded binary data from the multi-digit, binary number combinations associated with each node of the signal constellation diagram, with a maximum of one bit difference between the multi-digit, binary number combinations in any adjacent node, thereby optimizing a bit error rate of the decoded binary data and a signal to noise ratio of the measured current levels.

20. The method of claim 19, wherein:
the particular ordered set of adjacent DNA bases includes eight possible combinations of adjacent pairs of DNA base types; and
the method further comprises mapping, using the computer processor, each of the eight possible combinations of adjacent pairs of DNA base types, respectively, to a respective node of the signal constellation diagram; wherein each of eight nodes of the signal constellation diagram mapped by the adjacent pairs of DNA base types has a maximum of two mapped node neighbors.

* * * * *